United States Patent [19]

Godfrey, Jr. et al.

[11] Patent Number: 5,525,726
[45] Date of Patent: Jun. 11, 1996

[54] PROCESS FOR THE PREPARATION OF AN ANTIVIRAL AGENT

[75] Inventors: Jollie D. Godfrey, Jr., Trenton; Richard H. Mueller, Ringoes; Thomas P. Kissick; Janak Singh, both of Lawrenceville, all of N.J.

[73] Assignee: E. R. Squibb & Sons, Inc., Princeton, N.J.

[21] Appl. No.: 150,308

[22] Filed: Nov. 12, 1993

Related U.S. Application Data

[60] Continuation-in-part of Ser. No. 961,805, Oct. 16, 1992, abandoned, which is a division of Ser. No. 770,191, Oct. 2, 1991, Pat. No. 5,185,463.

[51] Int. Cl.$^6$ .................... C07B 57/00; C07D 473/18; A61K 31/52
[52] U.S. Cl. ............................... 544/276; 562/124
[58] Field of Search ............................... 544/276

[56] References Cited

U.S. PATENT DOCUMENTS

| | | | |
|---|---|---|---|
| 4,499,079 | 2/1985 | Gordon et al. | 546/170 |
| 5,064,961 | 11/1991 | Bisacchi et al. | 544/276 |
| 5,126,345 | 6/1992 | Slusarchyk et al. | 514/254 |
| 5,153,352 | 10/1992 | Norbeck et al. | 562/427 |
| 5,235,052 | 8/1983 | Pariza | 544/276 |

FOREIGN PATENT DOCUMENTS

| | | |
|---|---|---|
| 335355 | 10/1989 | European Pat. Off. . |
| 358154 | 3/1990 | European Pat. Off. . |
| 366059 | 5/1990 | European Pat. Off. . |
| 433897 | 6/1991 | European Pat. Off. . |

OTHER PUBLICATIONS

Ichikawa, JCS Chem Comm 1989, 1919–1921.
Yamamoto, J. Antibiotics 1989, 1854–1859.
Braitman, Antimicro Agents and Chemotherapy 35, pp. 1464–1468 (1991).
Norbeck, J Med Chem 33, 1281–1285 (1990).
Clement, Transplantation Proc. 23, (3), Supp 3, pp. 159–161 (1991).
Doering et al., "Stereochemistry Of The Methylenecyclopropane Rearrangement", Tetrahedron, vol. 26, pp. 2825–2835 (1970).
Ettlinger et al., "The Cis–Isomer of Feist's Acid", Chemistry and Industry, 1957, p. 891.
Bottini et al., "The Nuclear Magnetic Resonance . . . ", J. Org. Chem., 1956, vol. 21, pp. 1169–1170.
Gajewski, "Hydrocarbon Thermal Degenerate . . . ", Jour. Amer. Chem. Soc., vol. 93, pp. 4450–4458 (1971).
SUCR–P, Chem. Abst., 84, 105082(r) (1975).
DeVos et al., J. Amer. Chem. Soc., 104, 4282 (1982).
Aldrich Catalog, 1992, pp. 774–775.

*Primary Examiner*—Mark L. Berch
*Attorney, Agent, or Firm*—Stephen B. Davis

[57] ABSTRACT

Racemic Feist's acid is treated with (R)-(+)-α-methylbenzylamine to yield (1R-trans)-3-methylene-cyclopropane-1,2-dicarboxylic acid, (R)-α-methylbenzyl-amine (1:1) salt. This salt can then be converted to (1R-trans)-3-methylene-1,2-cyclopropanedicarboxylic acid, dimethyl ester which is an intermediate in the preparation of the antiviral agent [1R-(1α,2β,3α)]-2-amino-9-[2,3-bis(hydroxymethyl)cyclobutyl]-1,9-dihydro-6H-purin-6-one. The improved process also enables the recovery of racemic Feist's acid from the resolution.

1 Claim, No Drawings

PROCESS FOR THE PREPARATION OF AN ANTIVIRAL AGENT

PRIOR APPLICATIONS

This application is a continuation-in-part of Ser. No. 961,805 filed Oct. 16, 1992, now abandoned, which is a division of Ser. No. 770,191 filed Oct. 2, 1991, now U.S. Pat. No. 5,185,463.

BACKGROUND OF THE INVENTION

The compound [ 1R- (1α, 2β, 3α) ] -2-amino-9- [ 2,3-bis (hydroxymethyl)cyclobutyl] -1,9-dihydro-6H-purin-6-one, i.e.,

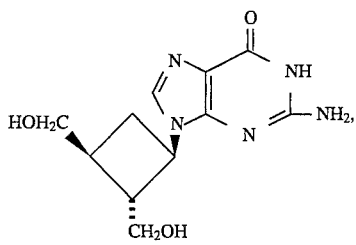

is an antiviral agent with activity against herpes simplex virus type 1 and 2, varicella zoster virus, and human cytomegalovirus.

Norbeck et al. in European Patent Application 366,059 describe the preparation of this and related purinyl and pyrimidinyl antiviral agents by several routes. One disclosed process utilizes the conversion of the optically pure compound of the formula

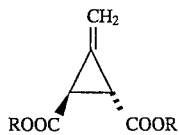

wherein R is an alkyl of 1 to 4 carbons as the starting material. This starting material is obtained by resolving the racemic Feist's acid with quinine according to literature procedures, e.g., W. von E. Doering et al., Tetrahedron, Vol. 26, p. 2825–2835 (1970).

Bisacchi et al. in U.S. patent application Ser. No. 451,664 filed Dec. 18, 1989, now U.S. Pat. No. 5,064,961 disclose preparing the antiviral agent [1R-(1α, 2β,3α)]-2- amino-9-[2,3-bis(hydroxymethyl)cyclobutyl]-1,9- dihydro-6H-purin-6-one from the intermediate

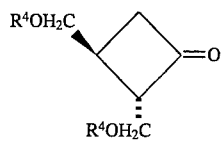

wherein $R^4$ is a protecting group such as benzoyl.

SUMMARY OF THE INVENTION

This invention is directed to an improved process for preparing the resolved intermediate of the formula

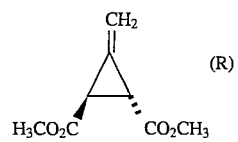

from the racemic starting material of the formula

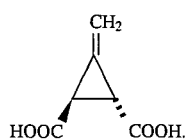

The process involves treating the racemic Feist's acid of formula II with (R)-(+)-α-methylbenzylamine to give the novel salt

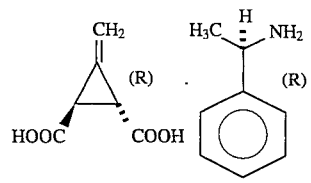

which is then converted to the resolved dimethyl ester of formula I.

This invention is also directed to the process by which the partially resolved (S)-Feist's acid obtained as a sideproduct in the above reaction is treated with (S)-(−)-α-methylbenzylamine to give the novel salt

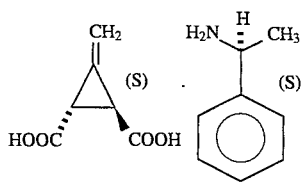

This salt is then converted to pure (S)-Feist's acid and then to the racemic starting material of formula II.

As a result, the processes of this invention enable the resolved starting material of formula I to be prepared more efficiently and economically.

DETAILED DESCRIPTION OF THE INVENTION

According to the process of this invention racemic Feist's acid of formula II is treated with (R)-(+)-α-methylbenzylamine in the presence of an alcohol solvent, i.e., isopropanol, and water at elevated temperature. Preferably the reaction is carried out at a temperature of about 75° C. Upon cooling, the (1R-trans)-3-methylenecyclopropane-1,2-dicarboxylic acid, (R)-α-methylbenzylamine (1:1) salt of formula III is readily obtained as a crystalline product.

The salt of formula III is then treated with acetyl chloride and methanol in the cold. The reaction mixture is allowed to warm to room temperature. Trimethyl orthoformate can be added to the reaction mixture to complete conversion of any monomethyl ester product to the desired dimethyl ester product of formula I.

An additional feature of this invention is the discovery that partially resolved Feist's acid containing an S:R ratio of about 80:20 can be separated from the mother liquor of the (R)-(+) -α-methylbenzylamine reaction. This is done by concentrating the mother liquor and partitioning the resulting semi-solid material between an acid such as 1N HCl and ethyl acetate. This partially resolved Feist's acid is then treated with (S)-(−) -α-methylbenzylamine in the presence of an alcohol solvent, i.e., isopropanol, at elevated temperature. Preferably the reaction is carried out at a temperature of about 70° C. Upon cooling, the (1S-trans)-3-methylenecyclopropane-1,2-dicarboxylic acid, (S)-α-methylbenzylamine (1:1) salt of formula IV is obtained as a crystalline material.

The salt of formula IV can then be converted to (S)-(−)- Feist's acid of the formula

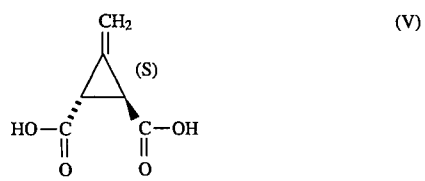

by treating an aqueous solution of the salt of formula IV with an acid such as in HCl and extracting with ethyl acetate.

The resulting (S)-(−)-Feist's acid of formula V can according to this invention be converted to the racemic Feist's acid starting material of formula II by treating an aqueous solution of the (S) acid of formula V with base such as 1N sodium hydroxide at an elevated temperature, preferably at about 100° C., followed by acidification such as with HCl and extraction with ethyl acetate.

Alternatively, the mother liquor from the resolution of racemic Feist's acid of formula II with (R)-(+)-α-methylbenzylamine can be treated to give the partially resolved salt of the formula

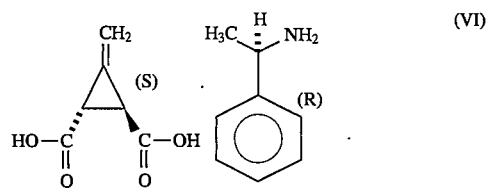

This partially resolved salt of formula VI can then be treated with aqueous sodium hydroxide and toluene. The aqueous fraction is heated at about 100° C. for about 18 hours and then cooled to room temperature. The resulting solution is adjusted to an acidic pH of about 2 and extracted to give a portion of the racemic Feist's acid starting material of formula II.

The (1R-trans)-3-methylene-1,2-cyclopropanedicarboxylic acid, dimethyl ester of formula I can be treated with a reducing agent to give the dimethanol compound of the formula

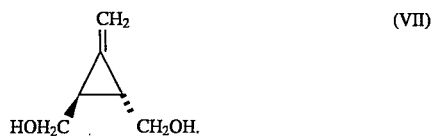

The dimethanol of formula VII can then be treated with a protecting reagent to give the compound of the formula

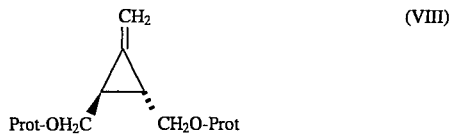

A suitable protecting agent is benzoic anhydride.

Treatment of the diprotected compound of formula VII I with 3-chloroperoxybenzoic acid gives the oxaspiro compound of the formula

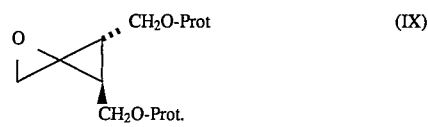

Treatment of the oxaspiro compound of formula IX with lithium iodide gives the cyclobutanone of the formula

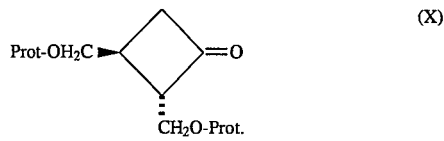

As taught by Bisacchi in U.S. application Ser. No. 451, 664, the cyclobutanone intermediate of formula X is treated with lithium trisiamylborohydride to give the cyclobutane compound of the formula

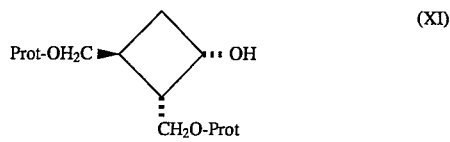

which is then treated with tosyl chloride to give the cyclobutane compound of the formula

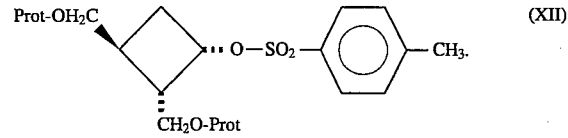

The tosyl compound of formula XII is then treated with the benzyloxy guanine of the formula

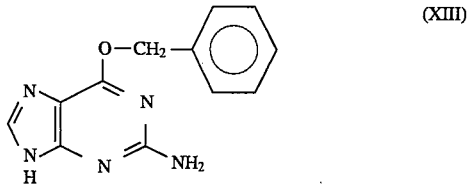

to give a compound of the formula

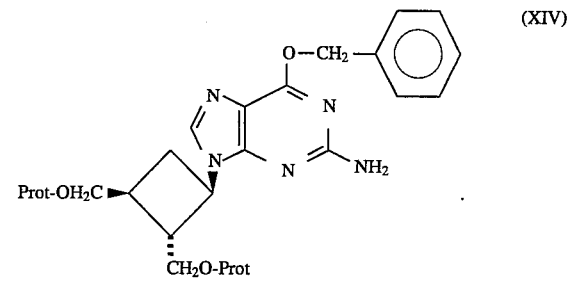

Removal of the protecting groups from the compound of formula XIV yields the antiviral agent [1R-(1α, 2β, 3α)]-2-amino-9-[2,3-bis(hydroxymethyl)cyclobutyl]-1,9-dihydro-6H-purin-6-one.

The following examples are illustrative of the processes of this invention.

EXAMPLE 1

[1R-(1α, 2α, 3α)]-2-Amino-9-[2,3-bis(hydroxymethyl)cyclobutyl]-1,9-dihydro-6H-purin-6-one a) (trans)-3-Methylene-1,2-cyclopropanedicarboxylic acid

A 2 l. three necked flask was equipped with a mechanical stirrer, thermocouple thermometer, and a heating mantle. The flask was charged with 7M sodium hydroxide (approx. 810 ml.) [234 g. sodium hydroxide plus water to approx. 810 ml.]. With stirring, the contents were heated to 104.5° C. To this hot alkali was added in about 10 g. portions finely powdered 3-bromo-4,6-dimethyl-2-oxo-2H-pyran -5-carboxylic acid, ethyl ester (135 g., 0.49 mole). After about 20 g. had been added the mixture was allowed to stir until the reaction color turned a dark red-brown. At this point, the addition of the powdered material was continued and the reaction temperature increased to 108°–109° C.

The reaction was then maintained at 100°–101° C. for an additional 30 minutes and then cooled to about 9° C. in an ice-salt bath. With cooling, the reaction mixture was adjusted to pH 2.0 by the addition of concentrated HCl (432 ml. required) while maintaining the temperature at less than 24° C. At a pH of about 5.4 foaming was observed and ethyl acetate (100 ml.) was added to prevent additional foaming as the pH was lowered.

The resulting mixture was extracted with ethyl acetate (2×600 ml.) and the pH of the aqueous fraction was adjusted to 2.0 by the addition of concentrated HCl (about 10 ml. required). The aqueous fraction was then extracted with ethyl acetate (2×400 ml.). The organic fractions were combined and washed with brine (2×500 ml.) and dried (MgSO$_4$). The solvent was removed at reduced pressure to give a dark brown solid which was then dried under high vacuum to give 63.73 g. of crude product.

The crude product was dissolved in water (445 ml.) with warming on a steam bath. To this solution was added decolorizing carbon (neutral Norit 6.3 g.). The resulting mixture was stirred at room temperature for 30 minutes and filtered through Celite. The water was evaporated at reduced pressure on a rotavap followed by drying under vacuum to give 59.61 g. of tan solid product.

This material (58.96 g.) was suspended with heating in ether (150 ml.). The resulting suspension was allowed to stand at room temperature for several hours and then refrigerated (about 4° C.). After standing in the cold for 6 days, the crystalline product was collected by filtration, washed with cold (−20° C.) ether, and dried under vacuum to give 34.85 g. of (trans)-3-methylene-1,2-cyclopropanedicarboxylic acid as a tan solid; m. p. 194°–196° C. (dec.). TLC (silica gel; dichloromethane:methanol:acetic acid, 18:1:1) R$_f$=0.24.

Anal. calc'd. for C$_6$H$_6$O$_4$: C, 50.71; H, 4.26
Found: C, 50.81; H, 4.40.

b) (1R-trans)-3-Methylenecyclopropane-1,2-dicarboxylic acid, (R)-α-methylbenzylamine (1:1) salt A mixture of the (trans)-3-methylene-1,2-cyclopropanedicarboxylic acid (70.89 g., 0.498 mole), isopropanol (660 ml.), and distilled water (71 ml.) was heated on a steam bath until a temperature of 75° C. was obtained. The resulting solution was removed from the steam bath. With stirring, (R)-(+)-α-methylbenzylamine (60.5 g., 0.499 moles) was added in approximately 2 ml. portions. The addition of the amine is exothermic and the temperature increased to 79° C. Additional isopropanol (50 ml.) was used to complete the transfer of the amine. The resulting solution was allowed to cool to room temperature slowly undisturbed. After about 15 minutes, while the solution was still hot, a small amount of seed crystals were added and crystallization commenced rapidly. After standing at room temperature overnight, the crystalline material was collected by filtration and washed with ice cold isopropanol (210 ml., 180 ml., 150 ml.). After most of the isopropanol had been removed, the crystalline material was slurried with heptane (200 ml.) and filtered. The material was dried under high vacuum to give 58.14 g. of tan solid. Rotations: 0.0113 g/2 ml H$_2$O (c=0.565; sonicate to obtain solution) $[\alpha]_{589}$=+86.1°, $[\alpha]_{578}$=+90.4°, $[\alpha]_{546}$=+103.1°, $[\alpha]_{436}$=+175.7°, $[\alpha]_{365}$=+273.2°.

This crude material (57.86 g.) was suspended in isopropanol (290 ml.; 5 ml/g) and water (87 ml.; about 1.5 ml/g). The resulting mixture was heated on a steam bath to a temperature of 82° C. At this point all of the material was not in solution and an additional portion of water (5 ml.) was added. After heating for 10 minutes an additional portion of water (5 ml.) was added and with continued heating a clear solution was obtained. To this hot solution was added, in 50 ml. portions, a total of 290 ml. of hot (80° C.) isopropanol with stirring. The resulting solution was allowed to cool slowly to room temperature and after 10 minutes a small amount of seed crystals were added. After standing at room temperature overnight, the crystalline product was collected by filtration and washed with ice cold isopropanol (2×100 ml., slurried). After most of the isopropanol had been removed the crystalline material was slurried with heptane (100 ml.) and filtered. The material was dried under high vacuum to give 46.31 g. of (1R-trans)-3 -methylenecyclopropane-1,2-dicarboxylic acid, (R)-α-methylbenzylamine (1:1) salt as a tan solid; m. p. 218°–223° C. (dec.).

Rotations: 0.0122 g/2 ml. H$_2$O (c=0.61; sonicate to obtain solution) $[\alpha]_{589}$=+94.7°, $[\alpha]_{578}$=+98.8°, $[\alpha]_{546}$=+112.6°, $[\alpha]_{436}$=+191.6°, $[\alpha]_{365}$=+299.0°, Anal. calc'd. for C$_{10}$H$_{12}$O$_4$ $_C$, 63.87; H, 6.51; N, 5.32
Found: C, 63.69; H, 6.44; N, 5.26.

c) (1R-trans)-3-Methylene-1,2-cyclopropanedicarboxylic acid, dimethyl ester A 1-liter, three-necked flask equipped with a digital thermometer, argon inlet, and pressure equalizing addition funnel was charged with methanol (600 ml.). After cooling to 1° C. using an ice bath, acetyl chloride (28 ml., 0.393 mole) was added dropwise over 11 minutes. The temperature increased to 10.4° C. The resulting solution was stirred for 45 minutes. To this cold (0.6° C.) solution was added (1R-trans)-3-methylenecyclopropane -1,2-dicarboxylic acid, (R)-α-methylbenzylamine (1:1) salt (79.48 g., 0.301 mole). After stirring for 15 minutes the cold bath was removed and the resulting solution was stirred at room temperature under argon for about 20 hours. TLC analysis showed the presence of a small amount of the mono methyl ester. Trimethyl orthoformate (70 ml., 0.64 mmole) was added (no exotherm observed) to complete esterification and the resulting mixture was stirred for an additional 5 hours. The resulting mixture was concentrated at reduced pressure on a rotavap (35° C. water bath) to afford an amber solid which was partitioned between ethyl acetate (800 ml.) and water (300 ml.). The ethyl acetate fraction was washed with 1N HCl (1×130 ml., 1×100 ml.). The HCl washes were combined and back extracted with ethyl acetate (150 ml.). The ethyl acetate fractions were combined and washed with 1N sodium bicarbonate (2×125 ml., 1×75 ml.) and brine. After drying ($MgSO_4$), the solvent was removed at reduced pressure to give an amber liquid which was distilled to give 51.05 g. of (1R-trans)-3-methylene-1,2-cyclopropanedicarboxylic acid, dimethyl ester; m. p. 34.1°–34.9° C. TLC (silica gel; hexane:ethyl acetate, 7:3) $R_f$=0.35.

Rotations: 0.01509 g/2 ml. $CCl_4$ (c=0.7545) $[\alpha]_D$=+124.8, $[\alpha]_{578}$=+130.1°, $[\alpha]_{546}$=+147.6°, $[\alpha]_{436}$=+245.0°, $[\alpha]_{365}$=+367.6°.

Anal. calc'd. for $C_8H_{10}O_4$: C, 56.47; H, 5.92
Found: C, 56.62; H, 5.90.

d) (1R-trans)-3-Methylene-1,2-cyclopropanedimethanol

A 1 liter, three-necked flask equipped with a mechanical stirrer, reflux condenser, pressure equalizing addition funnel, and an argon inlet was charged with 1.0M tetrahydrofuran solution of lithium aluminum hydride (200 ml.). To this solution was added dropwise, over 25 minutes, a solution of (1R-trans)-3-methylene-1,2-cyclopropanedicarboxylic acid, dimethyl ester (17 g., 100 mmol.) in dry tetrahydrofuran (80 ml.). The addition was exothermic. An additional portion of tetrahydrofuran (20 ml.) was used to complete the addition. The resulting mixture was gently refluxed for 30 minutes and then cooled to 8° C. An additional portion of tetrahydrofuran (20 ml.) was added and the cooling bath was removed. The reaction was quenched by the cautious sequential addition of water (8 ml.) [vigorous gas evolution], 15% aqueous sodium hydroxide (8 ml.), and water (24 ml.). A white, semi-gelatinous material was obtained which was heated at reflux for 10 hours giving a solid. Anhydrous $MgSO_4$ (25 g.) was added and after stirring for several minutes the resulting mixture was filtered and the filter cake was washed twice with tetrahydrofuran. The filtrate was concentrated at reduced pressure to give a colorless oil which was dried under high vacuum for one hour to give 11.53 g. of crude product.

An analytical sample was obtained by distillation (3.5 g.; bulb to bulb) to give 3.44 g. of (1R-trans)-3-methylene-1,2-cyclopropanedimethanol as a colorless solid; m. p. 36.5°–37.4° C. TLC (silica gel; ethyl acetate:methanol, 8.5:15) $R_f$=0.47. Rotations: 0.02007 g/2ml methanol (c=1.00) $[\alpha]_D$=–6.5°, $[\alpha]_{578}$=–6.9°, $[\alpha]_{546}$=–8.0°, $[\alpha]_{436}$=–17.5°, $[\alpha]_{365}$= –39.7°.

Anal. calc'd. for $C_6H_{10}O_2$: C, 63.14; H, 8.83
Found: C, 63.21; H, 9.09.

e) (1R-trans)-3-Methylene-1,2-cyclopropanedimethanol, dibenzoate ester

To a solution of (1R-trans)-3-methylene-1,2-cyclopropanedimethanol (28.97 g., 0.2538 mole) in ethyl acetate (450 ml.) at 8° C. under argon was added benzoic anhydride (123.45 g., 0.545 mole, 2.15 eq.) and triethylamine (90 ml., 0.645 mole, 2.54 eq.). With the reaction being cooled in an ice bath, dimethylaminopyridine (1.55 g., 12.68 mmol., 0.05 eq.) was added. The reaction turned a yellow color and an exotherm was observed. After 10 minutes the ice bath was removed and the reaction was stirred at room temperature. After 5 hours, an additional portion of benzoic anhydride (6.0 g., 26.5 mmol., 0.1 eq.) and triethylamine (6.0 ml., 43 mmol., 0.17 eq.) was added. After stirring for 19 hours, TLC showed the reation to be complete. Water (9.0 ml.) was added and the resulting homogeneous solution was stirred at room temperature. After stirring for about 27 hours, the reaction mixture was diluted with ethyl acetate (900 ml.) and washed with water (2×200 ml.). The aqueous fractions were combined and extracted with ethyl acetate (100 ml.). The organic fractions were combined and washed with 1N HCl (2×150 ml.), 1N sodium bicarbonate (2×150 ml.), and brine (150 ml.). After drying ($MgSO_4$), the solvent was removed at reduced pressure and the residue chased with hexane (2×250 ml.). The resulting material was dried under high vacuum for 42 hours to give the crude product as a very pale yellow oil which crystallized rapidly when seeded to yield 81.1 g.

A sample of this crude product (2.0 g.) was dissolved in hot hexane (10 ml.) containing ethyl acetate (4 drops). After cooling to near room temperature the solution was seeded. After standing for several hours the material was refrigerated (about 4° C.). After 12 hours, the material was placed in a freezer (about –20° C.). After 10 hours at –20° C., the crystalline product was collected by filtration, washed with cold (–20° C.) hexane, and dried under vacuum to give 1.88 g. of (1R-trans)-3-methylene-1,2-cyclopropanedimethanol, dibenzoate ester; m. p. 54.3°–54.4° C. TLC (silica gel; hexane: ethyl acetate, 7:3) $R_f$=0.46.

Rotations: 0.04221 g/2 ml. $CCl_4$ (c=2.11) $[\alpha]_D$=–58.2°, $[\alpha]_{578}$=–60.7°, $[\alpha]_{546}$=–69.7°, $[\alpha]_{436}$=–127.0°, $[\alpha]_{365}$=–221.5°

Anal. calc'd. for $C_{20}H_{18}O_4$ C, 74.52; H, 5.63
Found: C, 74.51; H, 5.77.

f) (4S-trans)-1-Oxaspiro[2.2]pentane-4,5-dimethanol, dibenzoate ester

3-Chloroperoxybenzoic acid (50 g., 50–60% water wet) was dissolved in dichloromethane (400 ml.) in a separatory funnel. The organic layer was separated from the small aqueous layer and dried with anhydrous $MgSO_4$ (about 70 g., stirred for about 10 minutes). The resulting dichloromethane solution was concentrated to 200 ml. at reduced pressure on a rotavap (bath temperature 35° C.). A white solid forms as the solution cools during concentration. The resulting suspension was warmed in the rotavap both to obtain a clear solution.

To the 3-chloroperoxybenzoic acid solution (3.0 ml.) was added acetic acid (5 ml.). To this solution was added an aqueous solution of sodium iodide (11 ml.; 6.0 g. of NaI in about 50 ml. of water). Iodine forms instantaneously. To this solution was added water (15 ml.) and dichloromethane (5 ml.; additional dichloromethane was added to keep the 3-chlorobenzoic acid in solution). With efficient stirring, the resulting solution was titrated with 0.0995N sodium thiosulfate solution until the solution was a very pale yellow color. At this point, about 1 ml. of a 1% starch solution was added. Dark blue color forms. The titration was continued until the blue color was discharged to give a colorless solution.

Titration #1:3.0 ml. of the 3-chloroperoxybenzoic acid solution required 51.7 ml. of 0.0995N sodium thiosulfate solution to yield 0.857M 3-chloroperoxybenzoic acid in dichloromethane.

Titration 02:3.0 ml. of the 3-chloroperoxybenzoic acid solution required 51.6 ml. of 0.0995N sodium thiosulfate solution to yield 0.855M 3-chloroperoxybenzoic acid in dichloromethane.

Average titer equaled 0.856M 3-chloroperoxybenzoic acid solution.

To (1R-trans)-3-methylene-1,2-cyclopropanedimethanol, dibenzoate ester (32.23 g., 0.1 mole) was added the 0.856M solution of 3-chloroperoxybenzoic acid in dichloromethane (183 ml., 156.6 mmole). The resulting solution was stirred at room temperature under argon. After about one hour the reaction mixture became cloudy as 3-chlorobenzoic acid began to precipitate. TLC analysis indicated the reaction was complete after stirring at room temperature for 29 hours. The resulting nearly colorless suspension was transferred to a separatory funnel containing hexane (400 ml.), 1N sodium bicarbonate (200 ml.), and water (50 ml.). Solvent used to complete the transfer to the separatory funnel was composed of hexane:dichloromethane (2:1). The resulting mixture was shaken vigorously to dissolve a white precipitate (pH of aqueous layer was 7.18). The organic fraction was then washed with 0.5N sodium thiosulfate: 1N sodium bicarbonate [composition of wash, volume, pH of aqueous layer after wash; 1:1, 200 ml., pH 7.38; 1:1, 200 ml., pH 7.50; 1:1, 200 ml., pH 7.56; 1:2, 150 ml., pH 7.76], 1N sodium bicarbonate (100 ml., pH 7.96), and brine. After drying (MgSO$_4$), the solvent was removed at reduced pressure to give the crude product as a pale yellow oil.

An analytical sample was obtained by recrystallization. Crude product (2.2 g.) was suspended in hexane (10 ml.). The resulting mixture was heated on a steam bath and ethyl acetate was added to obtain a solution. Upon cooling slowly the material oiled out. The solvent composition was adjusted to keep the material in solution at room temperature [final solvent mixture, hexane (15.2 ml.) and ethyl acetate (3.5 ml.)]. Seed crystals were added and the mixture was placed in a refrigerator (4° C). After about 14 hours in the refrigerator, the crystalline product was collected by filtration, washed with ice cold hexane:ethyl acetate (10:1) and dried under vacuum to give 1.07 g. of (4S-trans)-1-oxaspiro[2.2] pentane -4,5-dimethanol, dibenzoate ester; m. p. 54.9°.

Rotations 0.02210 g/2 ml. CCl$_4$ (c=1.10) $[\alpha]_D$=−66.5°, $[\alpha]_{578}$=−68.9°, $[\alpha]_{546}$=−78.5°, $[\alpha]_{436}$=−134.1°, $[\alpha]_{365}$=−213.4°.

Anal. calc'd. for $C_{20}H_{18}O_5$: C, 71.00; H, 5.36
Found: C, 70.76; H, 5.46.

g) (2S-trans)-2,3-Bis[(benzyloxy) methyl]cyclobutanone

A 1-liter three necked flask equipped with a mechanical stirrer, internal thermocouple thermometer, and an argon inlet was charged with crude (4S-trans)-1-oxaspiro]2.2]pentane-4,5-dimethanol, dibenzoate ester (98.84 mmol) and ethyl acetate (500 ml.). The resulting solution was cooled to −6.7° C. with an ice-salt bath. To this cold solution was added, in one portion, anhydrous lithium iodide (13.0 g., 97.1 mmol.). The reaction mixture immediately turned brown and a rapid exotherm was observed. After stirring for 4 minutes, the ice-salt bath was replaced with an ice bath. After stirring for an additional 45 minutes the ice bath was removed and the reaction mixture was allowed to warm slowly. After 80 minutes the mixture was washed with 0.4M sodium thiosulfate: 1N sodium bicarbonate (2:5, 2×100 ml.), 1N sodium bicarbonate (100 ml.) and brine (slow phase split). After drying (MgSO$_4$), the solvent was removed at reduced pressure to give crude product as a cream colored solid which was dried under vacuum, 32.40 g.

This crude product was dissolved, with heating on a steam bath, in isobutyl acetate (60 ml.). A clear yellow solution was obtained. With efficient stirring, hot (about 80° C.) isooctane (220 ml.) was added and a clear solution was obtained. The mixture was seeded at 75° C. and the material crystallized rapidly at 70° C. After standing for 6 hours the mixture was placed in a refrigerator (+4° C.). After 14 hours at +4° C. the mixture was placed in a freezer (−20° C.). After one hour the crystalline product was collected by filtration and washed with cold (−20° C.) isooctane:isobutyl acetate (4:1) and isooctane (room temperature). The material was dried under vacuum to give 28.64 g. of (2S-trans)-2,3-bis [(benzyloxy)methyl]cyclobutanone as a nearly colorless solid; m. p. 96.7° C. TLC (silica gel; toluene:ether, 85:15) $R_f$=0.41.

Rotations: 0.02085 g/2 ml. CHCl$_3$ (c=1.043) $[\alpha]_D$=+24.1°, $[\alpha]_{578}$=+25.6°, $[\alpha]_{546}$=+28.9°, $[\alpha]_{436}$=+46.3°, $[\alpha]_{365}$=+55.9°.

Anal. calc'd. for $C_{20}H_{18}O_5$: C, 71.00; H, 5.36
Found: C, 70.75; H, 5.31.

The following steps are described by Bisacchi et al. in U.S. application Ser. No. 451,664 filed Dec. 18, 1989 U.S. Pat. No. 5,064,961.

h) [1S-(1α, 2β, 3β)]-3-hydroxy-1,2-cyclobutanedimethanol, 1,2-dibenzoate ester (2S-trans)-2,3-Bis[(benzoyloxy)methyl]cyclobutanone (33.81 g.) in 440 ml of dry tetrahydrofuran at −78° C. under argon was treated with 100 ml. of 1M lithium trisiamylborohydride in tetrahydrofuran over 20 minutes. After stirring another 10 minutes at −78° C., the mixture was warmed to room temperature, and 100 ml. of saturated sodium bicarbonate was added over 5 minutes. The resultant mixture was cooled in an ice-acetone bath and treated with 36.5 ml. of 30% hydrogen peroxide at a rate so as to maintain the temperature at 25°–30° C. After the addition, the mixture was diluted with 300 ml. of water and extracted with 1.1 L of ethyl acetate. The organic phase was washed with water (×3), dried over sodium sulfate, and concentrated to a colorless oil (35 g.). The oil was taken up in 100 ml. of hexane/ethyl acetate (2/1) and filtered through a 1L pad of silica gel(K-60), eluting with the same solvent mixture. Evaporation of the pure fractions gave 27 g. of pure title compound as a colorless oil. Another 4.4 g. of slightly impure material gave 3.4 g. of pure title compound after column chromatography in the same solvent mixture.

i)[1S-(1α, 2β, 3β)]-3 [[(4-Methylphenyl)sulfonyl]-oxy]-1,2-cyclobutanedimethanol, dibenzoate ester 1S-(1α, 2β, 3β)]-3-hydroxy-1,2-cyclobutanedimethanol, 1,2-dibenzoate ester (27 g.) was dissolved in 110 ml. of dry pyridine under argon and treated with p-toluenesulfonyl chloride (16.7 g.). The mixture was heated and stirred at 60° C. for 16 hours, cooled to 40° C. and treated with 2 ml. of water. After stirring for 2 hours at 40° C. the mixture was concentrated in vacuo to an oil. After azeotroping with 2×150 ml. of water in vacuo, the residue was partitioned between water and ethyl acetate. The organic phase was washed with water (×2), saturated sodium bicarbonate (×2), and brine. Drying over sodium sulfate and evaporation in vacuo gave 32.2 g. of an oil. Trituration with pentane gave 28.3 g. of a solid. Crystallization from ethyl acetate/pentane gave 18.4 g. of pure title compound as a solid m. p. 91°–92° C., $[\alpha]_D=+13.8°$ (c=1.3, CHCl$_3$). Another 4 g. of title compound was obtained by chromatography of the mother liquors on silica gel using hexane/ethyl acetate (3/1).

j) [1S-(1α, 2β, 3α)]-3-[2-Amino-6-(phenylmethoxy) -9H-purin-9-yl]-1,2-cyclobutanedimethanol, dibenzoate ester A mixture of dry 2-amino-6-benzyloxyguanine (13.4 g.), [1S-(1α,2β, 3β)]-3[[(4-methylphenyl)sulfonyl]oxy]-1,2-cyclobutanedimethanol, dibenzoate ester, (18.33 g.), powdered anhydrous potassium carbonate (10.22 g., dried over phosphorus pentoxide in vacuo at 130° C. for 72 hours), and 18-crown-6 (9.8 g.) in 495 ml. of dry dimethylformamide was stirred and heated at 110° C. under argon for 21 hours. The mixture was cooled to room temperature and filtered, and the filtrate was evaporated in vacuo to an oil which was partitioned between ethyl acetate and water. The organic phase was washed twice with water, dried over sodium sulfate, and evaporated to a foam (24.4 g.). Chromatography on silica gel in hexane/ethyl acetate (1/1) gave 10.7 g. of the title compound as a foam with $[\alpha]_D=-9.0°$ (c=0.67, CHCl$_3$).

k) [1R-(1α, 2β, 3α)]-2-Amino-9-[2,3-bis(hydroxymethyl) -cyclobutyl]-1,9-dihydro-6H-purin-6-one A solution of [1S-(1α, 2β, 3α)]-3-[2-amino -6-(phenylmethoxy)-9H-purin-9-yl]-1,2-cyclobutanedimethanol, dibenzoate ester (20.0 g.) in 550 ml. of methanol under argon was treated with 5 ml. of 25% sodium methoxide in methanol and heated at 40° C. for 2 hours. Aqueous hydrochloric acid (3N, 275 ml.) was then added to the reaction mixture, and heating was continued at 50° C. for 2 hours. This mixture was concentrated to 100 ml. and the solution was transferred to a separatory funnel, with addition of another 100 ml. of water. The solution was extracted with ether (3×100 ml.) and the pH of the aqueous layer was adjusted to 8.5 with the slow addition of 360 ml. of 2N potassium hydroxide. The resulting thick precipitate was filtered and the damp solid was recrystallized by dissolving in 200 ml. of hot water, filtering while hot, and chilling at 5° C. overnight. Drying in vacuo over phosphorus pentoxide gave 7.65 g. of an impure white solid. Chromatography on 750 ml. of CHP-20P resin with gradient elution using acetonitrile and water, concentration of the pertinent product fractions until turbid, and chilling this turbid solution for 1 hour at 0° C. gave crystals which were filtered. Drying in vacuo at room temperature over phosphorus pentoxide gave 6.3 g. of the title compound as a white crystalline solid, m. p. >270° C., $[\alpha]_D=-27°$ (c=1.0, DMSO).

EXAMPLE 2

(trans)-3-Methylene-1,2-cyclopropanedicarboxylic acid a) (1S-trans)-3-Methylenecyclopropane-1,2, -dicarboxylic acid, (S)-α-methylbenzyl -amine (1:1) salt The mother liquor obtained from the resolution of (trans)- 3-methylene-1,2-cyclopropanedicarboxylic acid (7.0 g.) with (R)-(+)-α-methylbenzylamine [See Example 1(b)] was concentrated at reduced pressure to give a dark amber semi-solid which was partitioned between 1N HCl (100 ml.) and ethyl acetate (100 mi.). The aqueous fraction was extracted with ethyl acetate (75, 75, 50 ml.) and the aqueous fraction discarded. The organic fractions were combined and washed with 1N HCl (50 ml.) and brine. After drying (MgSO$_4$), the solvent was removed at reduced pressure to give 3.6 g. of partially resolved (S)-(−)-Feist's acid as a light tan solid. Rotation 0.0162 g/2 ml. absolute ethanol (c=0.81) $[\alpha]_{589}=-111.3°$, $[\alpha]_{578}=-115.9°$, $[\alpha]_{546}=-131.3°$. Optical purity was approximately 72%.

The mother liquor obtained from the resolution of an additional portion of (trans)-3-methylene-1, 2-cyclopropanedicarboxylic acid (8.65 g.) with (R)-(+)-α-methylbenzylamine was treated as described above to give 4.74 g. of partially resolved (S)-(−)-Feist's acid as a brown solid. Rotations 0.0161 g/2ml. absolute ethanol (c=0.805) $[\alpha]_{589}=-88.3°$, $[\alpha]_{578}=-93.0°$, $[\alpha]_{546}=-105.4°$. Optical purity was approximately 58%.

The partially resolved (S)-(−)-Feist's acid from above [8.20 g., 57.7 mmol.; approximately 83:17(S:R)] was dissolved in isopropanol (70 ml.) and water (8.20 ml.) by heating on a steam bath. To the resulting solution at about 70° C. was added (S)-(−)-α-methylbenzylamine (7.0 g., 57.7 mmol.). The addition of the amine was exothermic. An additional portion of isopropanol (12 ml.) was used to complete the addition of the amine. The resulting dark amber solution was allowed to cool to room temperature. After about 1 hour no crystals had formed and the solution was placed in a refrigerator (4° C.). After about 30 minutes the solution was scratched and a rapid crystallization ensued. The resulting mixture was heated to 80° C. on a steam bath to redissolve the crystalline material; however, the material would not completely dissolve. The resulting mixture was allowed to cool to room temperature. After standing overnight, the crystalline material was collected by filtration and washed with cold (0° C.) isopropanol (2×25 ml., 1×25 ml.). The material was then dried under high vacuum to give 10.9 g. of crude product as a light tan, fluffy solid. Rotations: 0.0110 g/2 ml. water (c=0.55; sonicate to obtain solution) $[\alpha]_{589}=-84.9°$, $[\alpha]_{578}=-89.1°$, $[\alpha]_{546}=-101.4°$, $[\alpha]_{436}=-172.0°$, $[\alpha]_{365}=-267.6°$.

This crude material (10.83 g.) was suspended in isopropanol (70 ml.) and water (21 ml.). The resulting mixture was heated on a steam bath until complete solution was obtained (temperature 78° C.). Additional isopropanol (35 ml.) was added slowly while maintaining the temperature at about 78° C. The resulting solution was allowed to cool to room temperature slowly. After standing at room temperature for 20 hours, the crystalline product was collected by filtration and washed with cold (0° C.) isopropanol (3×20 ml.). The material was then dried under high vacuum to give 7.91 g. of (1S-trans)-3-methylene -cyclopropane-1,2-dicarboxylic acid, (S)-α-methylbenzylamine (1:1) salt as a straw colored crystalline solid; m. p. 218.4°–220.0° C. (dec.).

Rotations: 0.0112 g/2ml. water (c=0.56; sonicate to obtain solution) $[\alpha]_{589}=-93.7°$, $[\alpha]_{578}=-97.5°$, $[\alpha]_{546}=-110.0°$, $[\alpha]_{436}=-188.4°$, $[\alpha]_{365}=-293.7°$.

Anal. Calc'd. for $C_6H_6O_4 \cdot C_8H_{11}N$: C, 63.87; H, 6.51; N, 5.32

Found: C, 64.02; H, 6.49; N, 5.19.

b) (1S-trans)-3-Methylenecyclopropane- 1,2-dicarboxylic acid (1S-trans)-3-Methylenecyclopropane-1,2-dicarboxylic acid, (S)-α-methylbenzylamine (1:1) salt (7.0 g., 26.58 mmol.) was dissolved in water (25 ml.) and 1N HCl (75 ml.). The resulting solution was extracted with ethyl acetate (4×75 ml.). The ethyl acetate fractions were combined and washed with 1N HCl (30 ml.) and brine. After drying (MgSO$_4$), the solvent was removed at reduced pressure to give 3.6 g. of (1S-trans)-3-methylenecyclopropane -1,2-dicarboxylic acid as a nearly colorless solid; m. p. 199.4°–199.7° C. TLC (silica gel; dichloromethane:methanol:acetic acid, 18:1:1) $R_f$= 0.20.

Rotations: 0.01473 g/2 ml. absolute ethanol (c=0.736) $[\alpha]_{589}$=–153.6°, $[\alpha]_{578}$=–159.9°, $[\alpha]_{546}$=–181.5°, $[\alpha]_{436}$=–303.4°, $[\alpha]_{365}$=–460.5°.

Anal. Calc'd. for $C_6H_6O_4$: C, 50.71; H, 4.26
Found: C, 50.87; H, 4.38.

c) (trans)-3-Methylene-1,2-cyclopropanedicarboxylic acid (1S-trans)-3-Methylenecyclopropane-1,2-dicarboxylic acid (2 mmol.) was treated with 1N sodium hydroxide solution (5 ml.) at 100° C. for 21 hours. The resulting solution was acidified with 1N HCl and extracted with ethyl acetate to yield (trans)-3-methylene-1,2-cyclopropanedicarboxylic acid which was found to be essentially racemic (51.9:48.1, S:R) by comparison of the optical rotations.

EXAMPLE 3

(trans)-3-Methylene-1,2-cyclopropanedicarboxylic acid a) (1S-trans)-3-Methylenecyclopropane-1,2 -dicarboxylic acid, (R)-α-methylbenzylamine (1:1) salt The mother liquor from the resolution of (trans)-3-methylene-1,2-cyclopropanedicarboxylic acid (1818 g., 12.79 mole) with (R)-(+)-α-methylbenzylamine (1551 g., 12.80 mole) was concentrated at reduced pressure to give a dark, semi-solid residue. Isopropanol (2000 ml.) was added and the mixture was heated to 50° C. with stirring until a uniform suspension was obtained. Ethyl acetate (1000 ml.) was added and the resulting suspension was stirred at room temperature for 1 hour. The mixture was filtered, washed with acetone, and dried to give 1452 g. of partially resolved (1S-trans)-3-methyl -cyclopropane-1,2-dicarboxylic acid, (R)-α-methylbenzylamine (1:1) salt as a tan solid.

The mother liquor from above was concentrated at reduced pressure to a thick syrup to which isopropanol was added. Acetone (3000 ml.) was added and the resulting suspension was filtered, washed with acetone, and dried to afford a second crop of 126.9 g. of partially resolved (1S-trans) -3-methylcyclopropane-1,2-dicarboxylic acid, (R)-α-methylbenzylamine (1:1) salt.

b) (trans)-3-Methylene-1,2-cyclopropanedicarboxylic acid

To the (1S-trans)-3-methylenecyclopropane -1,2-dicarboxylic acid, (R)-α-methylbenzylamine (1:1) salt (500 g., 1.9 mole) was added 1.5N aqueous sodium hydroxide (3167 ml., 4.75 mole) and toluene (1000 ml.). After stirring, the phases were separated and the aqueous fraction was extracted with toluene (1×600 ml., 1×400 ml.). The organic fractions were set aside for recovery of the (R)-(+)-α-methylbenzylamine. The aqueous fraction was heated to reflux for 18.5 hours and then cooled to room temperature. The resulting solution was adjusted to pH 1.95 by the addition of concentrated HCl (364 ml.) and extracted with ethyl acetate (1×1200 ml., 1×1000 ml., 1×800 ml., 1×600 ml.). The organic fractions were combined, dried over anhydrous MgSO$_4$ and concentrated at reduced pressure to give 222.9 g. of racemic (trans)-3-methylene-1,2-cyclopropanedicarboxylic acid.

What is claimed is:

1. A process of preparing the aniviral agent [1R-(1α, 2β, 3α)]-2-amino-9-[2,3-bis(hydroxymethyl)cyclobutyl]-1,9-dihydro-6H-purin-6-one which comprises a) reacting racemic (trans)-3-methylene-1,2-cyclopropanedicarboxylic acid with (R)-(+)-α-methylbenzylamine in the presence of isopropanol and water at an elevated temperature, cooling the resulting solution to room temperature, and collecting the crystalline precipitate of (1R-trans) -3-methylenecyclopropane-1,2-dicarboxylic acid, (R)-α-methylbenzylamine (1:1) salt from the mother-liquor;

b) concentrating the mother-liquor from the reaction of step (a) to give a semi-solid residue which is then taken up in isopropanol and heated to give a suspension which is extracted with ethyl acetate and dried to give the partially resolved salt (1S-trans)-3-methylenecyclopropane-1,2-dicarboxylic acid, (R)-α-methylbenzylamine (1:1) salt;

c) treating the partially resolved salt product from step (b) with aqueous sodium hydroxide and toluene, separating the aqueous phase, heating to about 100° C. for about 18 hours, cooling to room temperature, adjusting the pH to about 2, extracting with ethyl acetate, and drying the organic fractions to recover racemic (trans)-3-methylene-1,2-cyclopropanedicarboxylic acid which is then employed as part of the starting material in step (a);

d) reacting the salt product from step (a) with acetyl chloride and methanol to give (1R-trans) -3-methylene-1,2-cyclopropanedicarboxylic acid, dimethyl ester;

e) reacting the dimethyl ester product from step (d) with a reducing agent to give (1R-trans)-3 -methylene-1,2-cyclopropanedimethanol;

f) reacting the dimethanol product from step (e) with a protecting reagent to give

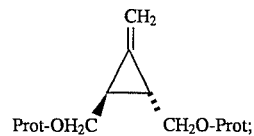

g) reacting the protected product from step (f) with 3-chloroperoxybenzoic acid to give the oxaspiro compound

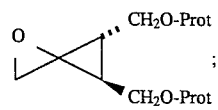

h) reacting the oxaspiro compound from step (g) with lithium iodide to give

15

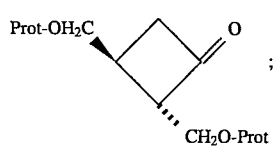

i) reacting the cyclobutanone product of step (h) with lithium trisiamylborohydride to give the cyclobutanol of the formula

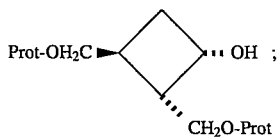

j) reacting the cyclobutanol product of step (i) with tosyl chloride to give the cyclobutane of the formula

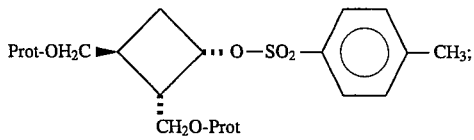

and

16 k) reacting the product of step (j) with benzyloxy guanine of the formula

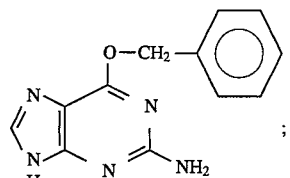

to give the compound of the formula

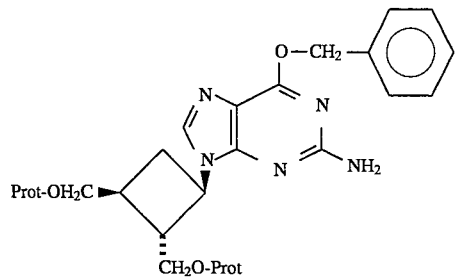

followed by removal of the benzyl and Prot protecting groups to give the desired final product.

* * * * *